United States Patent
Nirogi et al.

(10) Patent No.: US 11,622,967 B2
(45) Date of Patent: Apr. 11, 2023

(54) METHOD OF TREATMENT WITH HISTAMINE-3 RECEPTOR INVERSE AGONIST

(71) Applicant: SUVEN LIFE SCIENCES LIMITED, Hyderabad-Telangana (IN)

(72) Inventors: Ramakrishna Nirogi, Hyderabad (IN); Anil Karbhari Shinde, Hyderabad (IN); Vijay Sidram Benade, Hyderabad (IN); Saivishal Daripelli, Hyderabad (IN); Pradeep Jayarajan, Hyderabad (IN); Jyothsna Ravula, Hyderabad (IN); Venkateswarlu Jasti, Hyderabad (IN)

(73) Assignee: SUVEN LIFE SCIENCES LIMITED, Hyderabad (IN)

( * ) Notice: Subject to any disclaimer, the term of this patent is extended or adjusted under 35 U.S.C. 154(b) by 85 days.

(21) Appl. No.: 17/059,429

(22) PCT Filed: Aug. 1, 2018

(86) PCT No.: PCT/IB2018/055769
§ 371 (c)(1),
(2) Date: Nov. 28, 2020

(87) PCT Pub. No.: WO2019/229509
PCT Pub. Date: Dec. 5, 2019

(65) Prior Publication Data
US 2021/0213026 A1    Jul. 15, 2021

(30) Foreign Application Priority Data
May 31, 2018   (IN) ............................ 201841020498

(51) Int. Cl.
*A61K 31/5377*   (2006.01)
*A61P 25/00*     (2006.01)

(52) U.S. Cl.
CPC .......... *A61K 31/5377* (2013.01); *A61P 25/00* (2018.01)

(58) Field of Classification Search
CPC .............................. A61K 31/5377; A61P 25/00
See application file for complete search history.

(56) References Cited

U.S. PATENT DOCUMENTS

2017/0260135 A1    9/2017   Nirogi et al.

FOREIGN PATENT DOCUMENTS

| CA | 2827567 A1 | 8/2012 | |
|---|---|---|---|
| EP | 1717235 A2 * | 11/2006 | ........... C07D 207/20 |
| WO | WO-2005097751 A2 * | 10/2005 | ........... C07D 213/38 |
| WO | WO-2012114348 A1 * | 8/2012 | .............. A61P 25/00 |
| WO | 2016027275 A1 | 2/2016 | |
| WO | 2018033848 A1 | 2/2018 | |
| WO | WO-2018033847 A1 * | 2/2018 | ............. A61K 31/27 |

OTHER PUBLICATIONS

Bliwise, Neurodegenerative Dis., vol. 6, suppl. 1A, pp. S16-S28, publ. 2004 (Year: 2004).*
European Patent Office, International Search Report, PCT/IB2018/0055769, dated Feb. 22, 2019, Netherlands.
Jian-Sheng Lin et al., An Inverse Agonist of the Histamine H3 Receptor Improves Wakefulness in Narcolepsy, Neurobiology of Disease, vol. 30, No. 1, Apr. 1, 2008, Amsterdam, NL.
European Patent Office, Written Opinion of the International Searching Authority, PCT/IB2018/0055769, dated Feb. 22, 2019, Germany.
European Patent Office, International Preliminary Report on Patentability, PCT/IB2018/0055769, dated Oct. 27, 2020, Germany.

* cited by examiner

*Primary Examiner* — Sarah Pihonak
(74) *Attorney, Agent, or Firm* — IpHorgan Ltd.

(57) ABSTRACT

The present invention provides new methods of treatment for narcolepsy, excessive daytime sleepiness, obstructive sleep apnea, circadian rhythm sleep disorders, sleep and vigilance disorders associated with Parkinson's disease, multiple sclerosis, dementia or attention deficit hyperactivity disorder by administering a therapeutically effect amount of histamine-3 receptor (H3R) inverse agonist, N-[4-(1-Cyclobutylpiperidin-4-yloxy)phenyl]-2-(morpholin-4-yl)acetamide or a pharmaceutically acceptable salt thereof. The present invention further provides use of the said compounds in the manufacture of medicament intended for the treatment of the disorders described herein.

17 Claims, 8 Drawing Sheets

**$p<0.01$, *$p<0.05$. one way ANOVA followed by Dunnett's post hoc test (n=8)

Results expressed as mean cumulative time spent in wake during first 4 hours period ± SEM.

*** $p<0.001$ Vs vehicle (Dunnett's post test; n=6-12/ group)

Results expressed as mean cumulative time spent in wake during first 4 hours period ± SEM.

**p<0.01 Vs vehicle (Unpaired t-test; n=5/ group)

Figure (4a) Wake

Figure (4b) REM sleep

Figure (4c): NREM sleep
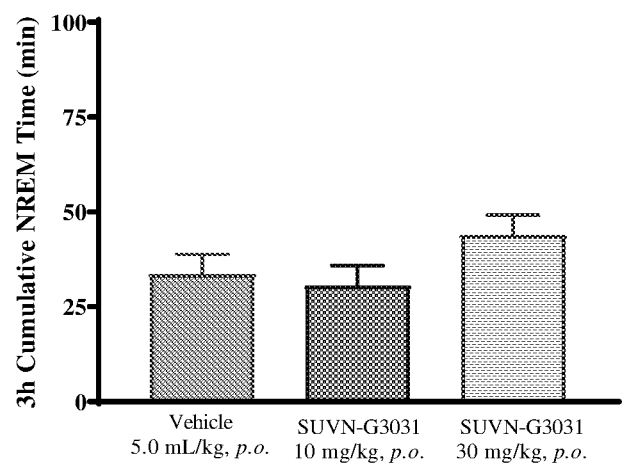
Results expressed as mean cumulative time spent in wake, REM or NREM during first 4 hours period ± SEM.
*$p<0.05$ Vs vehicle (Dunnett'spost test; n=7-8/ group)

Results expressed as mean ± SEM of DREMS observed during 4 hours period (n=7-8/group).

Results are cumulative changes in histamine levels expressed as mean area under the curve (AUC) ± S.E.M.

$*p<0.05$, $**p<0.01$ Vs Vehicle (Dunnett's test; n=6-8/ group).

Results are cumulative changes in dopamine and norepineprine levels expressed as mean area under the curve (AUC) ± S.E.M.

*$p<0.05$, **$p<0.01$ Vs Vehicle (Dunnett's test).

METHOD OF TREATMENT WITH HISTAMINE-3 RECEPTOR INVERSE AGONIST

FIELD OF THE INVENTION

The present invention provides new methods of treatment for narcolepsy, excessive daytime sleepiness, obstructive sleep apnea, circadian rhythm sleep disorders, sleep and vigilance disorders associated with Parkinson's disease, multiple sclerosis, dementia or attention deficit hyperactivity disorder by administering a therapeutically effect amount of histamine-3 receptor ($H_3R$) inverse agonist, N-[4-(1-Cyclobutylpiperidin-4-yloxy)phenyl]-2-(morpholin-4-yl)acetamide or a pharmaceutically acceptable salt thereof. The present invention further provides use of the said compounds in the manufacture of medicament intended for the treatment of the disorders described herein.

BACKGROUND OF THE INVENTION

Narcolepsy is a chronic neurological disorder involves a decreased ability to regulate sleep-wake cycles and is characterized by excessive daytime sleepiness and abnormal rapid eye movement (REM) sleep manifestations, including cataplexy (sudden loss of muscle tone triggered by strong emotions), direct transition from wakefulness to REM sleep (DREMs) periods, sleep paralysis and hypnagogic hallucinations (Lancet 369: 499-511). A common cause of narcolepsy is defective hypocretin/orexin transmission, either as a result of mutations in the hypocretin/orexin receptor 2 or a loss in ligand production (Neurobiol Dis 2001; 8:525-34). Further the narcolepsy is classified into, type 1 narcolepsy (or narcolepsy associated with cataplexy) is related to loss of hypocretin/orexin-producing neurons with low or undetectable hypocretin/orexin A levels in cerebrospinal fluid (CSF), type 2 narcolepsy (or narcolepsy not associated with cataplexy) is related to normal levels of hypocretin/orexin A in CSF (Nat Sci Sleep. 2015; 7:159-169) and narcolepsy due to medical condition.

The people with narcolepsy will experience irresistible attacks of sleep at any time during the day and if the urge becomes overwhelming, people with narcolepsy will fall asleep for period lasting from seconds to few hours. The narcoleptic sleep episodes can occur without any warning, which may be dangerous if the patients are driving, walking on road or operating a machine. These symptoms of narcolepsy cause a significant decrease in the quality of life for the narcoleptic individuals. Sleep disturbances such as excessive daytime sleepiness, insomnia, sleep fragmentation and circadian dysrhythmia and disorders of sleep initiation and maintenance are common in patients with neurodegenerative disorders like Parkinson's disease, multiple sclerosis, Alzheimer's disease and other forms of dementia like Lewy body dementia, Frontotemporal dementia, vascular dementia etc. (Psychogeriatrics 2015; 15, 65-74; Neurol Sci. 2013; 34: 1291-1296).

Histaminergic innervation of the central nervous system arises solely from the tuberomammillary nucleus in the posterior hypothalamus. Activation of histaminergic pathways produces wakefulness while decreased histaminergic activity results in sleepiness. Histamine follows a diurnal rhythm with high levels during wakefulness and lower levels during sleep. This is the result of integration of a number of signals from different sources which culminate to produce a wake promoting effect with circadian variation. Histamine also plays an integral role in regulation of orexin/hypocretin pathways, which are known as having strong wake promoting effects (CNS NeurolDisord Drug Targets 2007; 6: 31-43). It was found that the histamine levels in CSF were lower in narcoleptic patients with and without low hypocretin/orexin levels compared to healthy volunteers (Sleep 2009; 32: 175-80). The brain wake-promoting system is also activated by histaminergic neurons via antagonism of the histamine-3 receptor, a histamine autoreceptor located pre-synaptically that controls histamine turnover by feedback inhibition of histamine synthesis and release (Drugs. 2013; 73(16):1771-1781). Antagonism of histamine $H_3$ receptor enhances synaptic histamine signaling on histamine $H_1$ receptors and promotes wakefulness (Neuropharmacology. 2016; 106:35-36).

Several of the histamine-3 receptor antagonists/inverse agonists have reported wake-promoting activity in preclinical species like mice (Biol Pharm Bull 31: 2163-2181; Curr Top Med Chem 8:988-1002). Histamine-3 receptor is associated with enhanced activity not only of histaminergic neurons but also of other ascending waking pathways like noradrenergic, cholinergic or dopaminergic neurons. The empirical evidences suggest that $H_3R$ antagonist/inverse agonist may have promising utility for the treatment of various sleep disorders including excessive daytime sleepiness disorder and narcolepsy (Neurobiol Dis 1:74-83.). Thus, $H_3R$ inverse agonist could be a potential drug candidate for the treatment of narcolepsy, excessive day time sleepiness, obstructive sleep apnea, shift work sleep disorder, circadian rhythm sleep disorders, sleep and vigilance disorders associated with Parkinson's disease, multiple sclerosis, dementia or attention deficit hyperactivity disorder.

Individuals suffering from sleep associated disorders may face the problems during their daily life. Therefore, in order to improve the quality of life and normalize the sleep/wake cycle, there is a need to develop the pharmaceutical therapies for the treatment of narcolepsy, excessive day time sleepiness, obstructive sleep apnea, shift work sleep disorder, circadian rhythm sleep disorders or sleep and vigilance disorders associated with Parkinson's disease, multiple sclerosis, dementia or attention deficit hyperactivity disorder. The $H_3R$ inverse agonist of the present invention has produced wake promoting effects by modulating the neurotransmitters required for the therapeutic efficacy. Hence it could be the potential treatment for narcolepsy, excessive day time sleepiness, obstructive sleep apnea, shift work sleep disorder, circadian rhythm sleep disorders, sleep and vigilance disorders associated with Parkinson's disease, multiple sclerosis, dementia or attention deficit hyperactivity disorder.

SUMMARY OF THE INVENTION

The objective of the present invention is to provide methods for the treatment of narcolepsy, excessive daytime sleepiness, obstructive sleep apnea, circadian rhythm sleep disorder, or sleep and vigilance disorders associated with Parkinson's disease, multiple sclerosis, dementia or attention deficit hyperactivity disorder.

In first aspect, the present invention relates to a method of treatment for narcolepsy, excessive daytime sleepiness, obstructive sleep apnea, circadian rhythm sleep disorder, or sleep and vigilance disorders associated with Parkinson's disease, multiple sclerosis, dementia or attention deficit hyperactivity disorder comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamideor a pharmaceutically acceptable salt thereof.

In another aspect, the present invention relates to a method of treating narcolepsy associated with cataplexy, narcolepsy not associated with cataplexy or narcolepsy due to medical condition, comprising administering to a patient in need thereof, a therapeutically effective amount of a histamine-3 receptor inverse agonist is N-[4-(1-Cyclobutylpiperidin-4-yloxy)phenyl]-2-(morpholin-4-yl)acetamideor a pharmaceutically acceptable salt thereof.

In another aspect, the present invention relates to a method of treating excessive daytime sleepiness comprising administering to a patient in need thereof, a therapeutically effective amount of a histamine-3 receptor inverse agonist is N-[4-(1-Cyclobutylpiperidin-4-yloxy)phenyl]-2-(morpholin-4-yl)acetamide or a pharmaceutically acceptable salt thereof.

In another aspect, the present invention relates to a method of treating obstructive sleep apnea comprising administering to a patient in need thereof, a therapeutically effective amount of a histamine-3 receptor inverse agonist is N-[4-(1-Cyclobutylpiperidin-4-yloxy)phenyl]-2-(morpholin-4-yl)acetamide or a pharmaceutically acceptable salt thereof.

In another aspect, the present invention relates to a method of treating circadian rhythm sleep disorders comprising administering to a patient in need thereof, a therapeutically effective amount of a histamine-3 receptor inverse agonist is N-[4-(1-Cyclobutylpiperidin-4-yloxy)phenyl]-2-(morpholin-4-yl)acetamide or a pharmaceutically acceptable salt thereof.

In another aspect, the present invention relates to a method of treating the sleep and vigilance disorders associated with Parkinson's disease, multiple sclerosis, dementia or attention deficit hyperactivity disorder comprising administering to a patient in need thereof, a therapeutically effective amount of a histamine-3 receptor inverse agonist is N-[4-(1-Cyclobutylpiperidin-4-yloxy)phenyl]-2-(morpholin-4-yl)acetamide or a pharmaceutically acceptable salt thereof.

In another aspect, the present invention relates to use of histamine-3 receptor inverse agonist is N-[4-(1-Cyclobutylpiperidin-4-yloxy)phenyl]-2-(morpholin-4-yl)acetamide or a pharmaceutically acceptable salt thereof in the manufacture of medicament for the treatment of narcolepsy, excessive daytime sleepiness, obstructive sleep apnea, circadian rhythm sleep disorders, sleep and vigilance disorders associated with Parkinson's disease, multiple sclerosis, dementia or attention deficit hyperactivity disorder In another aspect, the present invention relates to a pharmaceutical composition for use in treatment of narcolepsy, excessive day time sleepiness, obstructive sleep apnea, shift work sleep disorder, circadian rhythm sleep disorders, sleep and vigilance disorders associated with Parkinson's disease, multiple sclerosis, dementia or attention deficit hyperactivity disorder comprising a histamine-3 receptor inverse agonist is N-[4-(1-Cyclobutylpiperidin-4-yloxy)phenyl]-2-(morpholin-4-yl)acetamide or a pharmaceutically acceptable salt thereof and pharmaceutically acceptable excipients thereof.

DETAILED DESCRIPTION

Figure 1A:
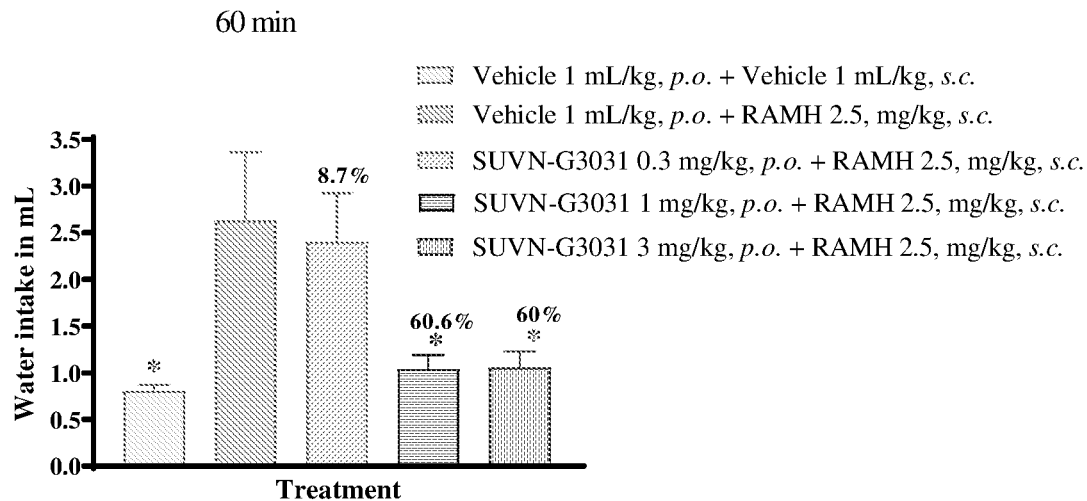
FIG. 1a: Effect of SUVN-G3031 on (R)-α-methylhistamine induced dipsogenia in rats. SUVN-G3031 was administered 60 min prior to (R)-α-methylhistamine.

Unless otherwise stated, the following terms used in the specification and claims have the meanings given below:

The term, "inverse agonist" as used herein refers to compounds that bind to the endogenous form of the receptor or to the constitutively activated form of the receptor and inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50% and most preferably by at least 75%, as compared with the baseline response in the absence of the inverse agonist.

Example of the histamine-3 receptor inverse agonist is N-[4-(1-Cyclobutylpiperidin-4-yloxy)phenyl]-2-(morpholin-4-yl)acetamideor a pharmaceutically acceptable salt thereof.

Examples of pharmaceutically acceptable salt of the above identified compound include but not limited to, N-[4-(1-Cyclobutylpiperidin-4-yloxy)phenyl]-2-(morpholin-4-yl)acetamidedihydrochloride.

The term, "narcolepsy" as used herein refers to a chronic neurological disorder characterized by recurring episodes of sleep during the day and it also referred as a rare long-term brain disorder that causes a person to suddenly fall asleep at inappropriate times. The brain is unable to regulate sleeping and waking patterns normally, which can result in irregular sleep features, overwhelming episodes of sleep, excessive daytime sleepiness, sleep attacks, cataplexy, sleep paralysis and excessive dreaming and waking in the night.

The term, "cataplexy" as used herein refers to reversible decrease or temporary loss of muscle control resulting in weakness and possible collapse, often in response to emotions such as laughter and anger. It may lead to slurred speech and buckling knees, or in more severe cases complete paralysis. The duration of the cataplectic attack, either partial or total, varies from few seconds to thirty minutes.

The term "narcolepsy associated with cataplexy or narcolepsy type 1" as used herein refers to combination of excessive daytime sleepiness and one or both of the following; a sudden loss of muscle tone while in awake or low or absent CSF hypocretin-1 (orexin) levels. It may lead to slurred speech and buckling knees, or in more severe cases complete paralysis. These events are usually triggered by strong emotions such as joy, surprise, laughter or anger. Narcolepsy type 1 is caused by a deficiency of hypocretin (orexin). A patient with low hypocretin has narcolepsy type 1, even if they do not exhibit cataplexy.

The term "narcolepsy not associated with cataplexy or narcolepsy type 2" as used herein refers to continuous excessive daytime sleepiness but no cataplexy and symptoms include patient have a nap for a couple of hours and after waking up feels refreshed, but after a short time, feel tired again.

The term "narcolepsy due to medical condition" as used herein refers to a group of disorders also known as secondary or symptomatic narcolepsy. Medical conditions commonly causing narcolepsy with cataplexy may betumors, sarcoidosis, arteriovenous malformations affecting the hypothalamus, multiple sclerosis plaques impairing the hypothalamus, paraneoplastic syndrome antt-Ma2 antibodies, Neimann-Pick type C disease or Coffin-Lowry syndrome. Medical condition commonly causing narcolepsy without cataplexy may be: head trauma, myotonic dystrophy, Prader-Willi syndrome, Parkinson's disease or multisystem atrophy.

The term, "obstructive sleep apnea" as used herein refers to a breathing disorder that occurs primarily during sleep with consequences that may persist throughout the waking hours in the form of sleepiness. This increasingly well-recognized disease is characterized by periodic collapse of the upper airway during sleep with apneas (periodic cessation of breathing), hypopneas (repetitive reduction in breathing) or a continuous or sustained reduction in ventilation and excessive daytime sleepiness, neurocognitive defects and depression. It affects almost every system in the body, resulting namely in increased incidence of cardiovascular disorders.

The term, "shift work sleep disorder" as used herein refers to a circadian rhythm sleep disorder characterized by insomnia and excessive sleepiness affecting people whose work hours overlap with the typical sleep period.

The term "circadian rhythm sleep disorder" as used herein refers to family of sleep disorders that are affecting the timing of sleep. People with circadian rhythm sleep disorders are unable to go to sleep and awaken at the times commonly required for work and school as well as social needs. Circadian rhythm sleep disorder of irregular sleep-wake type, is a rare form of circadian rhythm sleep disorders and it is characterized by numerous naps throughout the 24-hour period, no main nighttime sleep episode and irregularity from day to day. Circadian rhythm sleep disorder of jet lag type is a condition in which different body cycles are temporarily out of sync with each other and with the day-night cycle, resulting from travel across time zones. Circadian rhythm sleep disorder of shift work type is a condition in which circadian rhythms are disturbed due to working during the body's natural sleep time, and the patient has serious difficulty in adjusting to the required schedule.

The term, "excessive daytime sleepiness" as used herein refers to feeling very drowsy throughout the day, and having difficulty concentrating and staying awake.

The term, "excessive dreaming and waking in the night" as used herein refers to dreams often come as you fall asleep (hypnogogic hallucinations) or just before or during waking (hypnopompic hallucinations).

The term, "sleep attacks" as used herein refers to falling asleep suddenly and without warning.

The term, "restless leg syndrome" as used herein refers to a neurological sleep disorder that makes an overwhelming urge to move legs. Restless legs syndrome makes it difficult to get comfortable enough to fall asleep. The symptoms are usually worse at night. Restless legs syndrome leads to fewer hours of sleep each night. Many people with severe cases get less than five hours of sleep per night. In milder cases, sleep is not much disturbed, though the sleep may be of poorer quality. The accumulated sleep loss from restless legs syndrome can make the person excessively sleepy during the daytime, cause irritability and make concentration difficult. This may have a major impact on professional and personal life. People with restless legs syndrome are more likely to have depression or anxiety.

The term, "REM behavior disorder" as used herein refers tothe paralysis that normally occurs during REM sleep is incomplete or absent, allowing the person to "act out" his or her dreams that are vivid, intense and violent.

The term, "posttraumatic stress disorder" as used herein refers to specific behaviors, including devastating sleep problems, associated with the results of suffered trauma. Sleep-wake disorders suffered by those with PTSD include obstructive sleep apnea, central sleep apnea, nightmare disorders and idiopathic hypersomnia, among others.

The term, "Autism" as used herein refers to Autism spectrum disorder is a range of conditions characterized by challenges with social skills, repetitive behaviors, speech and nonverbal communication, as well as by unique strengths and differences. Autistic people experience hypersomnia caused by the additional stress.

The term, "Down Syndrome" as used herein refers to is a genetic disorder caused by the presence of all or part of a third copy of chromosome 21. Incidence of narcolepsy is higher in Down syndrome than in normal population The term, "Periodic Limb Movements" as used herein refers to a sleep disorder where the patient moves limbs involuntarily during sleep, and has symptoms or problems related to the movement.

The term, "Kleine-Levin syndrome" as used herein refers to a rare disease characterized by recurrent episodes of hypersomnia and to various degrees, behavioral or cognitive disturbances, compulsive eating behavior, and hypersexuality.

The term, "Parkinson's disease" as used herein refers to a neurodegenerative disorder, associated with a degeneration of dopaminergic neurons in the nigrostriatal tract which results in the motor impairments and neuropsychiatric disorders characteristic of the disease. Furthermore, Parkinson's disease patients have the sleep and vigilance disorders in addition to problem of movement initiation and control.

The "sleep and vigilance disorders" include excessive daytime sleepiness including sleep attacks, disorders of sleep initiation, maintenance of sleep, sleep disordered breathing, sleep apnea, parasomnia and circadian dysrhythmia.

The term, "dementia" as used herein refers to a group of symptoms associated with a decline in memory or other thinking skills severe enough to reduce a person's ability to perform everyday activities. Dementia is classified into dementia due to Alzheimer's disease, Lewy body dementia, vascular dementia, dementia due to Parkinson's disease, Frontotemporal dementia, Creutzfeldt-Jakob disease, mixed dementia and/or senile dementia. Furthermore, dementia patients may also have the sleep and vigilance disorders.

The term, "multiple sclerosis" as used herein refers to a chronic progressive disease affecting the central nervous system and is a potentially disabling disease of the brain and spinal cord.

The term, "attention deficit hyperactivity disorder" as used herein refers to is a chronic condition marked by persistent inattention, hyperactivity, and sometimes impulsivity and begins in childhood and often lasts into adulthood.

The term, "therapeutically effective amount" is defined as an amount of a compound/medicament of the present invention that (i) is effective in producing the desired therapeutic effect (ii) treats the particular disease, condition or disorder, (iii) eliminates one or more symptoms of the particular disease, condition or disorder and (iv) delays the onset of one or more symptoms of the particular disease, condition or disorder described herein.

The term, "pharmaceutically acceptable salt" as used herein refers to salts of the active compound and are prepared by reaction with the appropriate organic or inorganic acid or acid derivative, depending on the particular substituents found on the compounds described herein. The pharmaceutically acceptable salt includes but not limited to, dimesylate, dihydrochloride salt, oxalate salt, succinate, tartrate salt and the like. Preferably, the pharmaceutically acceptable salt is dihydrochloride and tartrate salts. More preferably, the pharmaceutically acceptable salt is dihydrochloride salt.

The term, "patient" as used herein refers to an animal. Preferably the term "patient" refers to mammal. The term mammal includes animals such as mice, rats, dogs, rabbits, pigs, monkeys, horses and human. More preferably the patient is human.

The compound as used herein is N-[4-(1-Cyclobutylpiperidin-4-yloxy)phenyl]-2-(morpholin-4-yl)acetamidedihydrochloride, (also referred as SUVN-G3031) which has the chemical structure,

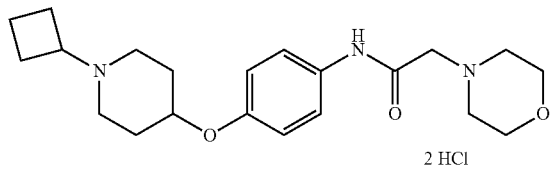

(I)

The compound, SUVN-G3031 and its preparation has been described in U.S. Pat. Nos. 9,079,888 and 9,802,896 respectively.

In the context of the invention, the term, "treatment" or 'treating" as used herein means any treatment of a disease in a mammal, including: (a) slowing or arresting the development of clinical symptoms; and/or (b) causing the regression of clinical symptoms.

The term, "compound for use" as used herein embrace any one or more of the following: (1) use of a compound, (2) method of use of a compound, (3) use in the treatment of, (4) the use for the manufacture of pharmaceutical composition/medicament for treatment/treating or (5) method of treatment/treating/preventing/reducing/inhibiting comprising administering an effective amount of the active compound to a patient in need thereof.

EMBODIMENTS

The present invention encompasses all the examples described herein without limitation, however, preferred aspects and elements of the invention are discussed herein in the form of the following embodiments.

In one embodiment, the present invention relates to the method of treatment for narcolepsy, excessive daytime sleepiness, obstructive sleep apnea, circadian rhythm sleep disorders, sleep and vigilance disorders associated with Parkinson's disease, multiple sclerosis, dementia or attention deficit hyperactivity disorder comprises administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In another embodiment, the present invention relates to the method of treating narcolepsy comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In another embodiment, the present invention relates to the method of treating narcolepsy associated with cataplexy or narcolepsy not associated with cataplexy or narcolepsy due to medical condition comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In one embodiment, the present invention relates to the method of treating narcolepsy associated with cataplexy comprises administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In one embodiment, the present invention relates to the method of treating narcolepsy not associated with cataplexy comprises administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In one embodiment, the present invention relates to the method of treating narcolepsy due to medical condition comprises administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In another embodiment, the present invention relates to the method of treating excessive daytime sleepiness comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In another embodiment, the present invention relates to the method of treating obstructive sleep apnea comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In another embodiment, the present invention relates to the method of treating excessive daytime sleepiness associated with narcolepsy, obstructive sleep apnea, restless leg syndrome, REM behavior disorder, posttraumatic stress disorder, autism and Down syndrome, menstrual related hypersomnia or Kleine-Levin syndrome comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In another embodiment, the present invention relates to the method of treating circadian rhythm sleep disorders selected from irregular sleep-wake type, jet lag type or shift work type comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In another embodiment, the present invention relates to the method of treating sleep and vigilance disorders associated with Parkinson's disease, multiple sclerosis, dementia or attention deficit hyperactivity disorder comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In another embodiment, the present invention relates to the method of treating sleep and vigilance disorders associated with dementia selected from Lewy body dementia, vascular dementia, dementia due to Parkinson's disease, dementia due to Alzheimer's disease, Frontotemporal dementia and/or senile dementia comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In preferred embodiment, the present invention relates to the method of treatment for narcolepsy, excessive daytime sleepiness, obstructive sleep apnea, shift work sleep disorder, circadian rhythm sleep disorders, sleep and vigilance disorders associated with Parkinson's disease, multiple sclerosis, dementia or attention deficit hyperactivity disorder comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the method of treating narcolepsy comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the method of treating narcolepsy associated with cataplexy, narcolepsy not associated with cataplexy or narcolepsy due to medical condition comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the method of treating narcolepsy associated with cataplexy comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the method of treating narcolepsy not associated with cataplexy comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the method of treating narcolepsy due to medical condition comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the method of treating excessive daytime sleepiness comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the method of treating obstructive sleep apnea comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the method of treating excessive daytime sleepiness associated with narcolepsy, obstructive sleep apnea, restless leg syndrome, REM behavior disorder, posttraumatic stress disorder, autism and Down syndrome, menstrual-related hypersomnia or Kleine-Levin syndrome comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the method of treating circadian rhythm sleep disorders selected from irregular sleep-wake type, jet lag type or shift work type comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the method of treating sleep and vigilance disorders associated with Parkinson's disease, multiple sclerosis, dementia or attention deficit hyperactivity disorder comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the method of treating sleep and vigilance disorders associated with dementia selected from Lewy body dementia, vascular dementia, dementia due to Parkinson's disease, dementia due to Alzheimer's disease, Frontotemporal dementia and/or senile dementia comprising administering to a patient in need thereof, a therapeutically effective amount of a histamine-3 receptor inverse agonist, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of N-[4-(1-Cyclobutylpiperidin-4-yloxy)phenyl]-2-(morpholin-4-yl)acetamide or a pharmaceutically acceptable salt thereof in the treatment of narcolepsy, excessive daytime sleepiness, obstructive sleep apnea, circadian rhythm sleep disorders, sleep and vigilance disorders associated with Parkinson's disease, multiple sclerosis, dementia or attention deficit hyperactivity disorder.

In yet another embodiment, the present invention relates to use of N-[4-(1-Cyclobutylpiperidin-4-yloxy)phenyl]-2-(morpholin-4-yl)acetamide or a pharmaceutically acceptable salt thereof in the treatment of narcolepsy.

In yet another embodiment, the present invention relates to use of N-[4-(1-Cyclobutylpiperidin-4-yloxy)phenyl]-2-(morpholin-4-yl)acetamide or a pharmaceutically acceptable salt thereof in the treatment of narcolepsy associated with cataplexy.

In yet another embodiment, the present invention relates to use of N-[4-(1-Cyclobutylpiperidin-4-yloxy)phenyl]-2-(morpholin-4-yl)acetamide or a pharmaceutically acceptable salt thereof in the treatment of narcolepsy not associated with cataplexy.

In yet another embodiment, the present invention relates to use of N-[4-(1-Cyclobutylpiperidin-4-yloxy)phenyl]-2-(morpholin-4-yl)acetamide or a pharmaceutically acceptable salt thereof in the treatment of narcolepsy due to medical condition.

In yet another embodiment, the present invention relates to use of N-[4-(1-Cyclobutylpiperidin-4-yloxy)phenyl]-2-(morpholin-4-yl)acetamide or a pharmaceutically acceptable salt thereof in the treatment of excessive daytime sleepiness.

In yet another embodiment, the present invention relates to use of N-[4-(1-Cyclobutylpiperidin-4-yloxy)phenyl]-2-(morpholin-4-yl)acetamide or a pharmaceutically acceptable salt thereof in the treatment of obstructive sleep apnea.

In yet another embodiment, the present invention relates to use of N-[4-(1-Cyclobutylpiperidin-4-yloxy)phenyl]-2-(morpholin-4-yl)acetamide or a pharmaceutically acceptable salt thereof in the treatment of excessive daytime sleepiness associated with narcolepsy, obstructive sleep apnea, restless leg syndrome, REM behavior disorder, posttraumatic stress disorder, autism and Down syndrome, menstrual-related hypersomnia or Kleine-Levin syndrome.

In yet another embodiment, the present invention relates to use of N-[4-(1-Cyclobutylpiperidin-4-yloxy)phenyl]-2-(morpholin-4-yl)acetamide or a pharmaceutically acceptable salt thereof in the treatment of circadian rhythm sleep disorders selected from irregular sleep-wake type, jet lag type or shift work type.

In yet another embodiment, the present invention relates to use of N-[4-(1-Cyclobutylpiperidin-4-yloxy)phenyl]-2-(morpholin-4-yl)acetamide or a pharmaceutically acceptable salt thereof, for use in the treatment of sleep and vigilance disorders associated with Parkinson's disease, multiple sclerosis, dementia or attention deficit hyperactivity disorder.

In yet another embodiment, the present invention relates to use of N-[4-(1-Cyclobutylpiperidin-4-yloxy)phenyl]-2-(morpholin-4-yl)acetamide or a pharmaceutically acceptable salt thereof, for use in the treatment of sleep and vigilance disorders associated with dementia selected from Lewy body dementia, vascular dementia, dementia due to Parkinson's disease, dementia due to Alzheimer's disease, Frontotemporal dementia and/or senile dementia.

In yet another embodiment, the present invention relates to use of N-[4-(1-Cyclobutylpiperidin-4-yloxy)phenyl]-2-(morpholin-4-yl)acetamide dihydrochloride in the treatment of narcolepsy, excessive daytime sleepiness, obstructive sleep apnea, shift work sleep disorder, circadian rhythm sleep disorders, sleep and vigilance disorders associated with Parkinson's disease, multiple sclerosis, dementia or attention deficit hyperactivity disorder.

In yet another embodiment, the present invention relates to use of N-[4-(1-Cyclobutylpiperidin-4-yloxy)phenyl]-2-(morpholin-4-yl)acetamide dihydrochloride in the treatment of narcolepsy.

In yet another embodiment, the present invention relates to use of N-[4-(1-Cyclobutylpiperidin-4-yloxy)phenyl]-2-(morpholin-4-yl)acetamide dihydrochloride in the treatment of narcolepsy associated with cataplexy.

In yet another embodiment, the present invention relates to use of N-[4-(1-Cyclobutylpiperidin-4-yloxy)phenyl]-2-(morpholin-4-yl)acetamide dihydrochloride in the treatment of narcolepsy not associated with cataplexy.

In yet another embodiment, the present invention relates to use of N-[4-(1-Cyclobutylpiperidin-4-yloxy)phenyl]-2-(morpholin-4-yl)acetamide dihydrochloride in the treatment of narcolepsy due to medical condition.

In yet another embodiment, the present invention relates to use of N-[4-(1-Cyclobutylpiperidin-4-yloxy)phenyl]-2-(morpholin-4-yl)acetamide dihydrochloride in the treatment of excessive daytime sleepiness.

In yet another embodiment, the present invention relates to use of N-[4-(1-Cyclobutylpiperidin-4-yloxy)phenyl]-2-(morpholin-4-yl)acetamide dihydrochloride in the treatment of obstructive sleep apnea.

In yet another embodiment, the present invention relates to use of N-[4-(1-Cyclobutylpiperidin-4-yloxy)phenyl]-2-(morpholin-4-yl)acetamide dihydrochloride in the treatment of excessive daytime sleepiness associated with narcolepsy, obstructive sleep apnea, restless leg syndrome, REM behavior disorder, posttraumatic stress disorder, autism and Down syndrome, menstrual-related hypersomnia or Kleine-Levin syndrome In yet another embodiment, the present invention relates to use of N-[4-(1-Cyclobutylpiperidin-4-yloxy)phenyl]-2-(morpholin-4-yl)acetamide dihydrochloride in the treatment of circadian rhythm sleep disorders selected from irregular sleep-wake type, jet lag type or shift work type.

In yet another embodiment, the present invention relates to use of N-[4-(1-Cyclobutylpiperidin-4-yloxy)phenyl]-2-(morpholin-4-yl)acetamide dihydrochloride in the treatment of sleep and vigilance disorders associated with Parkinson's disease, multiple sclerosis, dementia or attention deficit hyperactivity disorder.

In yet another embodiment, the present invention relates to use of N-[4-(1-Cyclobutylpiperidin-4-yloxy)phenyl]-2-(morpholin-4-yl)acetamide dihydrochloride in the treatment of sleep and vigilance disorders associated with dementia selected from Lewy body dementia, vascular dementia, dementia due to Parkinson's disease, dementia due to Alzheimer's disease, Frontotemporal dementia and/or senile dementia.

In yet another embodiment, the present invention relates to use of a histamine-3 receptor inverse agonist in the manufacture of a medicament for the treatment of narcolepsy, excessive daytime sleepiness, obstructive sleep apnea, circadian rhythm sleep disorders, sleep and vigilance disorders associated with Parkinson's disease, multiple sclerosis, dementia or attention deficit hyperactivity disorder, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of narcolepsy, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of narcolepsy associated with cataplexy or narcolepsy not associated with cataplexy or narcolepsy due to medical condition, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of narcolepsy associated with cataplexy, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of narcolepsy not associated with cataplexy, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of narcolepsy due to medical condition, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of excessive daytime sleepiness, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of obstructive sleep apnea, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of excessive daytime sleepiness associated with narcolepsy, obstructive sleep apnea, restless leg syndrome, REM behavior disorder, posttraumatic stress disorder, autism and Down syndrome, menstrual-related hypersomnia or Kleine-Levin syndrome, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of circadian rhythm sleep disorders selected from irregular sleep-wake type, jet lag type or shift work type, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of sleep and vigilance disorders associated with Parkinson's disease, multiple sclerosis, dementia or attention deficit hyperactivity disorder, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of sleep and vigilance disorders associated with dementia selected from Lewy body dementia, vascular dementia, dementia due to Parkinson's disease, dementia due to Alzheimer's disease, Frontotemporal dementia and/or senile dementia, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In yet another embodiment, the present invention relates to use of a histamine-3 receptor inverse agonist in the manufacture of a medicament for the treatment of narcolepsy, excessive daytime sleepiness, obstructive sleep apnea, circadian rhythm sleep disorders, sleep and vigilance disorders associated with Parkinson's disease, multiple sclerosis, dementia or attention deficit hyperactivity disorder, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of a histamine-3 receptor inverse agonist in the manufacture of a medicament for the treatment of narcolepsy, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of a histamine-3 receptor inverse agonist in the manufacture of a medicament for the treatment of narcolepsy associated with cataplexy, narcolepsy not associated with cataplexy or narcolepsy due to medical condition, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of a histamine-3 receptor inverse agonist in the manufacture of a medicament for the treatment of narcolepsy associated with cataplexy, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of a histamine-3 receptor inverse agonist in the manufacture of a medicament for the treatment of narcolepsy not associated with cataplexy, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of a histamine-3 receptor inverse agonist in the manufacture of a medicament for the treatment of narcolepsy due to medical condition, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of a histamine-3 receptor inverse agonist in the manufacture of a medicament for the treatment of excessive daytime sleepiness, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of a histamine-3 receptor inverse agonist in the manufacture of a medicament for the treatment of obstructive sleep apnea, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of a histamine-3 receptor inverse agonist in the manufacture of a medicament for the treatment of excessive daytime sleepiness associated with narcolepsy, obstructive sleep apnea, restless leg syndrome, REM behavior disorder, posttraumatic stress disorder, autism and Down syndrome, menstrual-related hypersomnia or Kleine-Levin syndrome, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of a histamine-3 receptor inverse agonist in the manufacture of a medicament for the treatment of circadian rhythm sleep disorders selected from irregular sleep-wake type, jet lag type or shift work type, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of a histamine-3 receptor inverse agonist in the manufacture of a medicament for the treatment of sleep and vigilance disorders associated with Parkinson's disease, multiple sclerosis, dementia or attention deficit hyperactivity disorder, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to use of a histamine-3 receptor inverse agonist in the manufacture of a medicament for the treatment of sleep and vigilance disorders of dementia selected from Lewy body dementia, vascular dementia, dementia due to Parkinson's disease, dementia due to Alzheimer's disease, Frontotemporal dementia and/or senile dementia, wherein the histamine-3 receptor inverse agonist is N-[4-(1-Cyclobutylpiperidin-4-yloxy)phenyl]-2-(morpholin-4-yl)acetamide dihydrochloride.

In yet another embodiment, the present invention relates to the combination of N-[4-(1-Cyclobutylpiperidin-4-yloxy)phenyl]-2-(morpholin-4-yl)acetamideor a pharmaceutically acceptable salt thereof with modafinil or a pharmaceutically acceptable salt thereof, for the treatment of narcolepsy, excessive daytime sleepiness, obstructive sleep apnea, shift work sleep disorder, circadian rhythm sleep disorders, sleep and vigilance disorders associated with Parkinson's disease, multiple sclerosis, dementia or attention deficit hyperactivity disorder.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, cosolvents, preservatives, wetting agents, thickening agents, antifoaming agents, sweetening agents, flavouring agents, antioxidants, colorants, solubilizers, plasticizer, dispersing agents and the like. Excipients are selected from microcrystalline cellulose, mannitol, lactose, pregelatinized starch, sodium starch glycolate, corn starch or derivatives thereof, povidone, crospovidone, calcium stearate, glycerylmonostearate, glycerylpalmitostearate, talc, colloidal silicone dioxide, magnesium stearate, sodium lauryl sulfate, sodium stearylfumarate, zinc stearate, stearic acid or hydrogenated vegetable oil, gum *arabica*, magnesia, glucose, fats, waxes, natural or hardened oils, water, physiological sodium chloride solution or alcohols, for example, ethanol, propanol or glycerol, sugar solutions, such as glucose solutions or mannitol solutions and the like or a mixture of the various excipients.

In yet another aspect, the active compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art.

In yet another aspect, the pharmaceutical composition of the instant invention contains 1 to 90%, 5 to 75% and 10 to 60% by weight of the compound of the instant invention or pharmaceutically acceptable salt thereof. The amount of the active compound or its pharmaceutically acceptable salt in the pharmaceutical composition(s) can range from about 0.1 mg to about 500 mg or from about 5 mg to about 400 mg or from about 5 mg to about 250 mg or from about 7 mg to about 150 mg or in any range falling within the broader range of 1 mg to 500 mg.

EXAMPLES

The examples given below are provided by the way of illustration only and therefore should not be construed to limit the scope of the invention.

| Abbreviations: | |
|---|---|
| ANOVA | Analysis of variance |
| AP | Anterior Posterior |
| aCSF | Artificial Cerebrospinal fluid |
| $CaCl_2 \cdot 2H_2O$ | Calcium chloride dihydrate |
| DREM | Direct transition of wake to REM sleep |
| DV | Dorsal Ventral |
| DTT | Dithiothreitol |
| $EC_{50}$ | Half maximal effective concentration |
| EDTA | Ethylene diamine tetraacetic acid |
| EMG | Electromyogram |
| EEG | Electroencephalogram |
| GTP | Guanosinetriphosphate |
| HCl | Hydrochloric acid |
| HEPES | 4-(2-Hydroxyethyl)piperazine-1-ethanesulfonic acid |
| h | Hour(s) |
| Hz | Hertz |
| $IC_{50}$ | Half maximal inhibitory concentration |
| Kg | Kilogram |
| $K_i$ | Inhibitory constant |
| KCl | Potassium chloride |
| LC-MS/MS | Liquid chromatography-Mass spectrometry/Mass spectrometry |
| mg | Milligram |
| $MgCl_2$ | Magnesium chloride |
| min | Minute(s) |
| ML | Medial Lateral |
| mM | Millimolar |
| nmol/L | Nanomoles per litre |
| NaCl | Sodium chloride |

-continued

| Abbreviations: | |
|---|---|
| ng | Nanogram |
| nM | Nanomolar |
| p.o. | Per oral |
| RAMH | (R)-α-methylhistamine |
| s.c. | Subcutaneous |
| S.E.M. | Standard error of the mean |
| µl | Microlitre |
| µM | Micromolar |
| θ | Theta |

Example 1: Determination of $K_i$ Value at Human and Rat Histamin-3 Receptor Histamine-3 membranes were prepared from recombinant CHO-k1 cells expressing human histamine-3 receptor or rat histamine-3 receptor. Radioligand (RS)-α-Methylhistamine [ring-1,2-3H] was purchased from American Radiolabeled chemicals (ARC) (Cat No. ART 1342). The final ligand concentration was 3 nM; non-specific determinant was Methyl histamine (100 µM) and histamine-3 membrane (60 µg/well). Methyl histamine was used as a positive control. Reactions were carried out in binding buffer 50 mMTris-HCl (pH 7.4) buffer containing 5 mM $MgCl_2$ for 60 minutes at 25° C. Incubation was stopped by rapid filtration followed by four washes of the binding mixture using 96 well harvest plate (Millipore Cat no. MSFCNXB50) pre coated with 0.5% polyethyleneimine. The plate was dried and the bound radioactivity collected on the filters was determined by scintillation counting using MicroBetaTriLux. Nonspecific binding was deducted from each data point. Radio ligand binding in the presence of non-labeled compound was expressed as a percent of the total binding and plotted against the log concentration of the compound. $K_i$ values were determined using GraphPad Prism 4 data analysis software package and curve-fitting program (GraphPad Software, Inc., San Diego, Calif.). Under these tested assay conditions $K_i$ value obtained for reference compound Methyl histamine in human and rat histamine-3 receptors are 3.45 nM and 2.62 nM respectively.

| Example | $K_i$ at Human $H_3$ | $K_i$ at Rat $H_3$ |
|---|---|---|
| SUVN-G3031 | 8.73 nM | 9.79 nM |

REFERENCE

1. Timothy W L et al., Molecular Pharmacology, 55: 1101-1107 (1999).

Example 2: Determination of $IC_{50}$ Value at Human Histamine-3 Receptor

Compound was tested at EurofinsCerepPanlabs according to the following procedures.
Materials and Methods:
Receptor source: Human recombinant expressed in CHO-K1 cells
Radioligand: [35S]-GTPγS
Vehicle: 1% DMSO
Reference agonist: R(−)-α-methylhistamine
Agonist concentration: 30 nM
Positive control: Thioperamide Incubation conditions: Reactions were carried out in 20 mM HEPES (pH 7.4) containing 100 mMNaCl, 10 mM $MgCl2$, 1 mM DTT, 1 mM EDTA for 30 minutes at 30° C. After incubation scintillation was measured on the luminescence counter and compared to the control values in order to ascertain any interactions of the test compound(s) with the cloned histamine-3 binding site.

Results:
The compound SUVN-G3031 exhibited inverse agonist functional nature. The $IC_{50}$ values are tabulated below.

| S. No. | Compound | $IC_{50}$ (nM) |
|---|---|---|
| 1 | Thioperamide (Positive control) | 140 |
| 2 | SUVN-G3031 | 20 |

REFERENCE

1. Laitinen J T and Jokinen M, J Neurochem. 71(2): 808-816 (1998)

Example 3: Dipsogenia Assay

The experiment consisted of 3 days. The animals were individually housed in their home cages. 24 h water consumption was recorded for 2 days. Rats were randomized according to average of 2 days water consumption. On the day of experiment, the rats were orally treated with vehicle and SUVN-G3031, 1 h later, animals were treated with either vehicle or R-α-methyl histamine (RAMH), 2.5 mg/kg, s.c. Water consumption was recorded for each animal at 60 min and 120 min post treatment of vehicle or R-α-methyl histamine by weighing each bottle to the nearest 0.1 g.

Statistical analysis: Data was compared and assessed by one-way ANOVA followed by Dunnett's post hoc test by using graph pad prism software package.

Figure 1B:
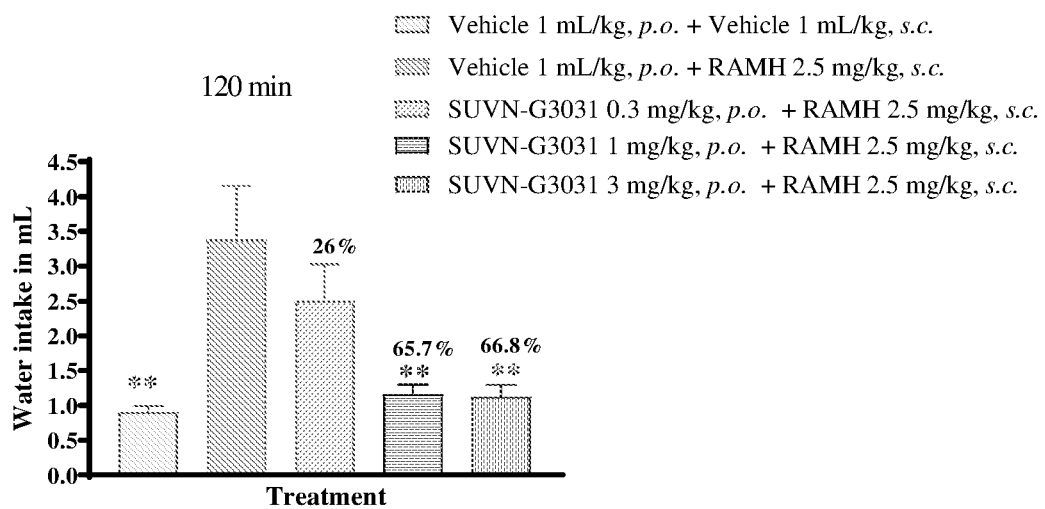
FIG. 1b: Effect of SUVN-G3031 on (R)-α-methylhistamine induced dipsogenia in rats. SUVN-G3031 was administered 120 min prior to (R)-α-methylhistamine.

Results: SUVN-G3031 blocked (R)-α-methylhistamine induced dipsogenia in rats at 60 min (FIG. 1a) and 120 min (FIG. 1b), indicating that SUVN-G3031 blocks histamine-3 receptor (in-vivo).

Example 4: Effect of SUVN-G3031 on Sleep and Wake Profile in Male Wistar Rats Using Telemetric Electroencephalogram (EEG) Recording Rats were anesthetized with isoflurane (Baxter India Private Limited; 4% in oxygen for induction; 2% for maintenance) and were fixed into the stereotaxic frame (Stoelting, Ill., USA) to perform surgery. An incision was made to reveal bregma from which coordinates were taken. Telemetric transmitter (Model F40-EET; DSI, St. Paul, Minn., USA) was implanted into intraperitoneal cavity of the rat and leads were tunneled subcutaneously to head. One pair of electrodes were implanted epidurally into the frontal cortex region using stainless steel screws (CMA Microdialysis, Stockholm, Sweden) at coordinates of AP+2.0 mm, ML±2.2 mm (Paxinos and Watson, 2004) for recording of EEG and electrodes were fixed to the skull with dental acrylic cement (DENTALON® plus). The second set of lead wires was implanted into the neck nuchal muscle to record electromyogram (EMG). Incision was closed using non absorbable sutures. After a surgical recovery of minimum 2 weeks, animals were acclimatized to the handling procedures and were given a mock dosing for 3 days before the first experimental day.

On the day of study, transmitter was switched on using magnet and animals were transferred on to the receiver along with the home cage. Recording was started 3 h after the lights-on using Ponemah (Version 5.2) software. After basal recording for 2 h, animals were treated with vehicle or SUVN-G3031 in a cross-over design with washout period of one week between doses. Recording was continued for 6 h post treatment. EEG and EMG were collected as primary signals and sampled at 500 Hz. Whereas, temperature and activity were sampled at 250 Hz. The data was stored for off-line analysis using NeuroScore software (Version 3.0).

Statistical analysis: EEG data was scored with automated standard sleep scoring protocols using Neuroscore. Rodent EEG and EMG data was manually classified into one of three sleep/wake states: awake, REM (Rapid eye movement/ Paradoxical sleep), or NREM (Non-rapid eye movement/ slow wave sleep) according to visual analysis of EEG frequency and amplitude characteristics and EMG activity using 10 s epochs. Waking activity was defined as relatively low-amplitude EEG activity with low power in the low-frequency bands, accompanied by moderate to high level EMG activity. NREM was defined as generally high-amplitude EEG activity with greater power in the low-frequency bands from 0.5-4 Hz, accompanied by minimal EMG activity. REM sleep was characterized by moderate and constant amplitude EEG activity focused in the 0 (6-9 Hz) range with no (or only sporadic) EMG activity. REM sleep was always preceded by NREM sleep. REM can be characterized by the ratio of theta and delta power which should be >1 and with no or minimal EMG activity.

Cumulative time spent in wake was calculated for first 4 hours post dosing of SUVN-G3031 and were compared against vehicle treatment using ANOVA and Dunnett's multiple comparison test. Statistical significance was considered at a p value less than 0.05. Each test group consisted of 6 to 12 rats.

Figure 2:
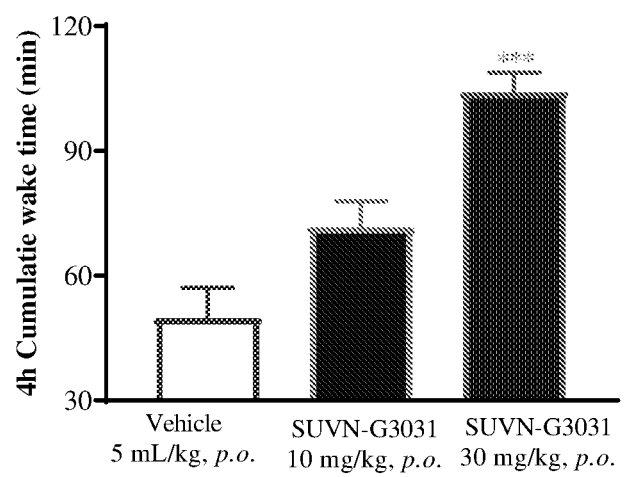
FIG. 2: Wake promoting effects of SUVN-G3031 in male Wistar rats.

Results: Treatment with SUVN-G3031 (10 and 30 mg/kg, p.o.) significantly increased the time spent in wake period compared to vehicle (FIG. 2) indicating that SUVN-G3031 will have beneficial effects in treatment of excessive daytime sleepiness

REFERENCES

1. Drutel G., Peitsaro N, Karlstedt K, Wieland K, Smit M J, Timmerman H, et al. Mol. Pharmacol 59, 1-8 (2001).
2. Paxinos G. and Watson C. (2004) Rat brain in stereotaxic coordinates. Academic Press, New York Example 5: Effect of SUVN-G3031 on Sleep and Wake Profile in Male C57BL/6J Mice Using Telemetric EEG Recording Mice were anesthetized with isoflurane (Baxter India Private Limited; 4% in oxygen for induction; 2% for maintenance) and were fixed into the stereotaxic frame (Stoelting, Ill., USA) to perform surgery. An incision was made to reveal bregma from which coordinates were taken. Telemetric transmitter (Model F20-EET; DSI, St. Paul, Minn., USA) was implanted into intraperitoneal cavity of the rat and leads were tunneled subcutaneously to head. One pair of flexible spring electrodes were implanted epidurally into the frontal cortex region at coordinates of AP+1.0 mm, ML±2.0 mm (Franklin and Paxinos, 20074) for recording of EEG and electrodes were fixed to the skull with dental acrylic cement (DENTALON® plus). The second set of lead wires was implanted into the neck nuchal muscle to record EMG. Incision was closed using non absorbable sutures. After a surgical recovery of minimum 2 weeks, animals were acclimatized to the handling procedures and were given a mock dosing for 3 days before the first experimental day.

On the day of study, transmitter was switched on using magnet and animals were transferred on to the receiver along with the home cage. Recording was started 3 h after the lights-on using Ponemah (Version 5.2) software. After basal recording for 2 h, animals were treated with vehicle or SUVN-G3031 in a cross-over design with washout period of one week between doses. Recording was continued for 6 h post treatment. EEG and EMG were collected as primary signals and sampled at 500 Hz. Whereas, temperature and activity were sampled at 250 Hz. The data was stored for off-line analysis using NeuroScore software (Version 3.0).

Statistical analysis: EEG data was scored with automated standard sleep scoring protocols using Neuroscore. Rodent EEG and EMG data was manually classified into one of three sleep/wake states: awake, REM (Rapid eye movement/ Paradoxical sleep), or NREM (Non-rapid eye movement/ slow wave sleep) according to visual analysis of EEG frequency and amplitude characteristics and EMG activity using 10 s epochs. Waking activity was defined as relatively low-amplitude EEG activity with low power in the low-frequency bands, accompanied by moderate to high level EMG activity. NREM was defined as generally high-amplitude EEG activity with greater power in the low-frequency bands from 0.5-4 Hz, accompanied by minimal EMG activity. REM sleep was characterized by moderate and constant amplitude EEG activity focused in the $\theta$ (6-9 Hz) range with no (or only sporadic) EMG activity. REM sleep was always preceded by NREM sleep. REM can be characterized by the ratio of theta and delta power which should be >1 and with no or minimal EMG activity.

Cumulative time spent in wake was calculated for first 4 hours post dosing of SUVN-G3031 and were compared against vehicle treatment using ANOVA and Dunnett's multiple comparison test. Statistical significance was considered at a p value less than 0.05. Each test group consisted of 5 mice.

Figure 3:
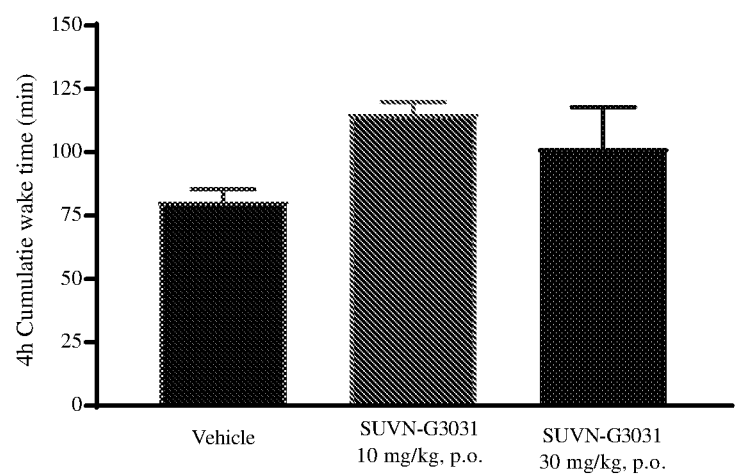
FIG. 3: Wake promoting effects of SUVN-G3031 in male C57BL6J mice.

Results: Treatment with SUVN-G3031 (10 and 30 mg/kg, p.o.) produced significant increase in the time spent in wake period compared to vehicle (FIG. 3) indicating that SUVN-G3031 will have beneficial effects in treatment of excessive daytime sleepiness.

REFERENCES

1. Drutel G., Peitsaro N, Karlstedt K, Wieland K, Smit M J, Timmerman H, et al. Mol. Pharmacol 59, 1-8 (2001).
2. Franklin K B J and Paxinos G. (2007) The mouse brain in stereotaxic coordinates. Academic Press, New York.

Example 6: Effect of SUVN-G3031 on Sleep and Wake Profile in Orexin-B-Saporin Lesioned Male Wistar Rats Using Telemetric EEG Recording Rats were anesthetized with 4% isoflurane (Baxter India Private Limited) and maintained on 2% isoflurane for entire duration of surgery. Under isoflurane anesthesia, rats were placed into a stereotaxic instrument and received bilateral microinjections of 0.5 μL containing 490 ng of orexin-B-saporin conjugate (Advanced Targeting System, San Diego, Calif., USA) or saline solution in the lateral hypothalamus (coordinates: AP: −3.5 mm; ML: ±1.5 mm; DV: −8.7 mm).[3] Microinjections were performed using a glass micropipette (20 µm at the tip). Analgesic and antibiotic treatment were administered at the end of this procedure.

After injection of the orexin-B-Saporin, telemetric transmitter (Model F40-EET; DSI, St. Paul, Minn., USA) was implanted into intraperitoneal cavity of the rat and leads were tunneled subcutaneously to head. One pair of electrodes were implanted epidurally into the frontal cortex region using stainless steel screws (CMA Microdialysis, Stockholm, Sweden) at coordinates of AP+2.0 mm, ML±2.2 mm (Paxinos and Watson, 2004)[3] for recording of EEG and electrodes were fixed to the skull with dental acrylic cement (DENTALON® plus). The second set of lead wires was implanted into the neck nuchal muscle to record EMG. Incision was closed using non absorbable sutures. After a surgical recovery of about 3 weeks, animals were acclimatized to the handling procedures and were given a mock dosing for 3 days before the first experimental day.

On the day of study, transmitter was switched on using magnet and animals were transferred on to the receiver along with the home cage. Recording was started 1 h before lights-off using Ponemah (Version 5.2) software. After basal recording for 45 min, animals were treated with vehicle or SUVN-G3031 in a cross-over design with washout period of one week between doses. Recording was continued for 8 h post treatment. EEG and EMG were collected as primary signals and sampled at 500 Hz. Whereas, temperature and activity were sampled at 250 Hz. The data was stored for off-line analysis using NeuroScore software (Version 3.0).

Statistical analysis: EEG data was scored with automated standard sleep scoring protocols using Neuroscore. Rodent EEG and EMG data was manually classified into one of three sleep/wake states: awake, REM (Rapid eye movement/ Paradoxical sleep), or NREM (Non-rapid eye movement/ slow wave sleep) according to visual analysis of EEG frequency and amplitude characteristics and EMG activity using 10 s epochs. Waking activity was defined as relatively low-amplitude EEG activity with low power in the low-frequency bands, accompanied by moderate to high level EMG activity. NREM was defined as generally high-amplitude EEG activity with greater power in the low-frequency bands from 0.5-4 Hz, accompanied by minimal EMG activity. REM sleep was characterized by moderate and constant amplitude EEG activity focused in the θ (6-9 Hz) range with no (or only sporadic) EMG activity. REM sleep was always preceded by NREM sleep. REM can be characterized by the ratio of theta and delta power which should be >1 and with no or minimal EMG activity.

Cumulative time spent in wake, REM and NREM stages were calculated for first 4 hours post dosing of SUVN-G3031 and were compared against vehicle treatment using ANOVA and Dunnett's multiple comparison test. Statistical significance was considered at a p value less than 0.05.

Figure 4:
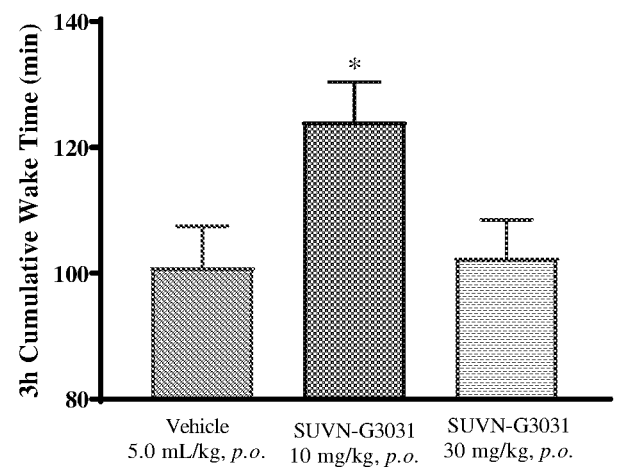
FIG. 4: Effect of SUVN-G3031 on wake (FIG. 4a) and sleep ((FIG. 4b—REM SLEEP) and (FIG. 4c—NREM sleep)) in orexin-B lesioned male Wistar rats.
Figure 4:
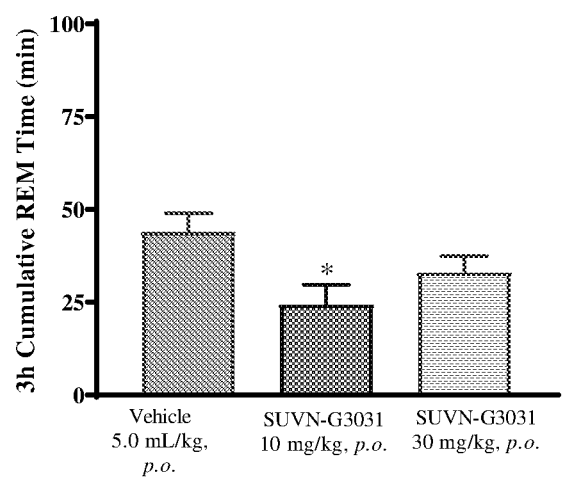
Figure 5:
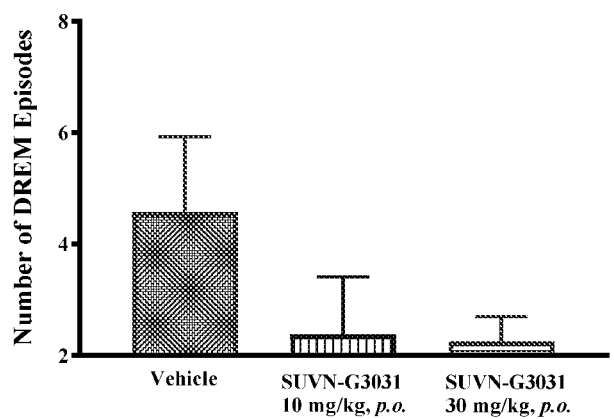
FIG. 5: Effect of SUVN-G3031 on direct transition from wake to REM sleep (DREM) in orexin-B lesioned male Wistar rats.

Results: In animal model of narcolepsy, SUVN-G3031 produced significant increase in wake period compared to vehicle (FIG. 4a). The treatment produced significant decrease in REM sleep in orexin-B-saporin lesioned rats (FIG. 4b). There was no effect observed on NREM sleep (FIG. 4c). Additionally, treatment produced decreased evidences of cataplectic (direct transition of wake to REM) episodes (FIG. 5). These results support the utility of SUVN-G3031 in treatment of disorders like narcolepsy with and without cataplexy.

REFERENCES

1. Drutel G., Peitsaro N, Karlstedt K, Wieland K, Smit M J, Timmerman H, et al. Mol. Pharmacol 59, 1-8 (2001).
2. Gerashchenko D, Kohls M D, Greco M, Waleh N S, Salin-Pascual R, Kilduff T S, Lappi D A, Shiromani P J. Hypocretin-2-saporin lesions of the lateral hypothalamus produce narcoleptic-like sleep behavior in the rat. J Neurosci. 21(18), 7273-7283 (2001).
3. Paxinos G. and Watson C. (2004) Rat brain in stereotaxic coordinates. Academic Press, New York.

Example 7: Evaluation of Histamine Modulation in Prefrontal Cortex of Male Wistar Rats Male Wistar rats (240-300 g body weight) were stereotaxically implanted with a microdialysis guide cannula in prefrontal cortex (PFC; AP: +3.2 mm, ML: −0.5 mm, DV: −1.0 mm) under isoflurane anesthesia. Co-ordinates were taken according to atlas for the rat brain (Paxinos and Watson 2004) with reference points taken from bregma and vertical from the skull. The rats were allowed to recover individually for four days in a round bottom Plexiglas bowl with free access to feed and water.

After surgical recovery of 4 days, male Wistar rats were connected to dual quartz lined two-channel liquid swivel (Instech, UK) on a counter balance lever arm, which allowed unrestricted movements of the animal. Sixteen hours before start of the study, a pre-equilibrated microdialysis probe (4 mm dialysis membrane) was inserted into PFC through the guide cannula. On the day of study, probe was perfused with artificial cerebrospinal fluid (aCSF; NaCl 147 mmol, KCl 2.7 mmol, $MgCl_2$ 1.0 mmol, $CaCl_2 \cdot 2H_2O$ 1.3 mmol) at a flow rate of 1.5 µL/min and a stabilization period of 2 h was maintained. Five basal samples were collected at 20 min intervals prior to the treatment of SUVN-G3031 or vehicle. Dialysate samples were collected for additional periods of 4 h. Dialysates were stored below −50° C. prior to analysis.

Quantitation of histamine: Histamine concentrations in dialysates were quantified using post-column derivatization with o-phthalaldehyde employing HPLC coupled to fluorescence detector and analysis was carried out in the calibration range of 33-640 fmol/20 µL Statistical analysis: All microdialysis data for histamine was plotted as percent change from mean dialysate basal concentrations with 100% defined as the average of five pre-dose values. The percent change in histamine levels were compared with vehicle using two-way analysis of variance (time and treatment), followed by Bonferroni's posttest. Area under the curve (AUC) values for percent change in histamine levels were calculated and the statistical significance between the mean AUC value were compared against vehicle treatment using one-way ANOVA followed by Dunnett's test. Statistical significance was considered at a p value less than 0.05. Incorrect probe placement was considered as criteria to reject the data from animal.

Figure 6:
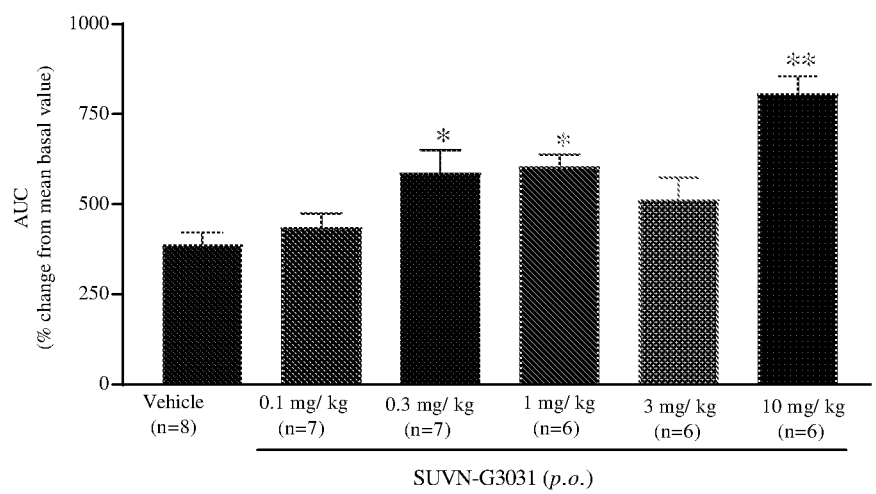
FIG. 6: Effect of SUVN-G3031 on histamine modulation in prefrontal cortex of male Wistar rats.

Results: Treatment with SUVN-G3031 (0.3-10 mg/kg, p.o.) produced significant increase in cortical histamine levels. Mean area under the curve values (AUC) calculated to assess the overall effect of treatment were statistically significant at 0.3, 1 and 10 mg/kg, p.o. of SUVN-G3031 as compared to vehicle treated group (FIG. 6).

REFERENCES

1. Drutel G., Peitsaro N, Karlstedt K, Wieland K, Smit M J, Timmerman H, et al. Mol. Pharmacol 59, 1-8 (2001).
2. Paxinos G. and Watson C. (2004) Rat brain in stereotaxic coordinates. Academic Press, New York.

Example 8: Evaluation of Dopamine and Norepinephrine Modulation in Prefrontal Cortex of Male Wistar Rats Male Wistar rats (240-300 g body weight) were stereotaxically implanted with a microdialysis guide cannula in prefrontal cortex (PFC; AP: +3.2 mm, ML: −0.5 mm, DV: −1.0 mm) under isoflurane anesthesia. Co-ordinates were taken according to atlas for the rat brain (Paxinos and Watson 2004) with reference points taken from bregma and vertical from the skull. The rats were allowed to recover individually for four days in a round bottom Plexiglas bowl with free access to feed and water.

After surgical recovery of 4 days, male Wistar rats were connected to dual quartz lined two-channel liquid swivel (Instech, UK) on a counter balance lever arm, which allowed unrestricted movements of the animal. Sixteen hours before start of the study, a pre-equilibrated microdialysis probe (4 mm dialysis membrane) was inserted into PFC through the guide cannula. On the day of study, probe was perfused with artificial cerebrospinal fluid (aCSF; NaCl 150 mmoL/L, $MgCl_2$ 0.9 mmoL/L, KCl 3 mmoL/L and $CaCl_2 \cdot 2H_2O$ 1.7 mmoL/L; pH 6.2) at a flow rate of 1.5 µL/min and a stabilization period of 2 h was maintained. Four basal samples were collected at 30 min intervals prior to the treatment of SUVN-G3031 or vehicle. Dialysate samples were collected for additional periods of 4 h. Dialysates were stored below −50° C. prior to analysis.

Quantitation of dopamine and norepinephrine: Monoamines in dialysate were derivatized with dansyl chloride and quantified using LC-MS/MS based method in calibration ranges of 0.07-15 nmol/L for all three analytes.

Statistical analysis: All microdialysis data for dopamine and norepinephrine were plotted as percent change from mean dialysate basal concentrations with 100% defined as the average of four pre-dose values. The percent change in neurotransmitter levels were compared with vehicle using two-way analysis of variance (time and treatment), followed by Bonferroni's posttest. Area under the curve (AUC) values for percent change in neurotransmitter levels were calculated and the statistical significance between the mean AUC value were compared against vehicle treatment using one-way ANOVA followed by Dunnett's test. Statistical significance was considered at a p value less than 0.05. Incorrect probe placement was considered as criteria to reject the data from animal.

Figure 7:
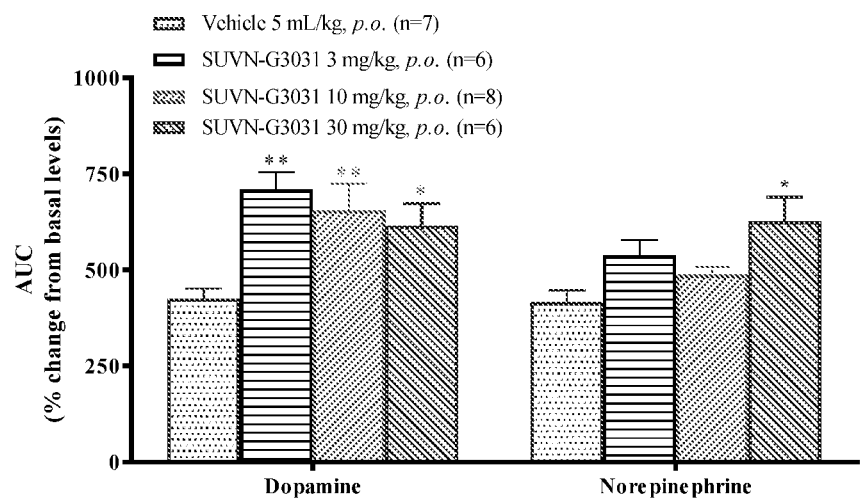
FIG. 7: Effect of SUVN-G3031 on dopamine and norepinephrine modulation in prefrontal cortex of male Wistar rats.

Results: Treatment with SUVN-G3031 (3-30 mg/kg, p.o.) produced significant increase in cortical levels of dopamine and norepinephrine in male Wistar rats (FIG. 7). These results further support the use of SUVN-G3031 in treatment of excessive daytime sleepiness associated with Parkinson's disease, attention deficit hyperactivity disorderand narcolepsy associated with and without cataplexy.

REFERENCE

1. Drutel G., Peitsaro N, Karlstedt K, Wieland K, Smit M J, Timmerman H, et al. Mol. Pharmacol 59, 1-8 (2001).
2. Paxinos G. and Watson C. (2004) Rat brain in stereotaxic coordinates. Academic Press, New York.

We claim:

1. A method of treating narcolepsy, excessive daytime sleepiness, circadian rhythm sleep disorders, or sleep and vigilance disorders associated with Parkinson's disease, multiple sclerosis, dementia or attention deficit hyperactivity disorder, comprising administering to a patient in need thereof, a therapeutically effective amount of a histamine-3 receptor inverse agonist, wherein the histamine-3 receptor inverse agonist is a compound, N-[4-(1-Cyclobutylpiperidin-4-yloxy)phenyl]-2-(morpholin-4-yl)acetamide or a pharmaceutically acceptable salt thereof.

2. The method as claimed in claim 1, wherein the pharmaceutically acceptable salt of N-[4-(1-Cyclobutylpiperidin-4-yloxy)phenyl]-2-(morpholin-4-yl)acetamide is selected from hydrochloride salt, oxalate salt, succinate salt and tartrate salt.

3. The method as claimed in claim 1, wherein the pharmaceutically acceptable salt of N-[4-(1-Cyclobutylpiperidin-4-yloxy)phenyl]-2-(morpholin-4-yl)acetamide is N-[4-(1-Cyclobutylpiperidin-4-yloxy)phenyl]-2-(morpholin-4-yl)acetamide dihydrochloride.

4. A method of treating narcolepsy as claimed in claim 1, comprising administering to a patient in need thereof, a therapeutically effective amount of a histamine-3 receptor inverse agonist is a compound, N-[4-(1-Cyclobutylpiperidin-4-yloxy)phenyl]-2-(morpholin-4-yl)acetamide or a pharmaceutically acceptable salt thereof.

5. A method of treating narcolepsy as claimed in claim 4, wherein the pharmaceutically acceptable salt is N-[4-(1-Cyclobutylpiperidin-4-yloxy)phenyl]-2-(morpholin-4-yl)acetamide dihydrochloride.

6. A method of treating as claimed in claim 4, wherein narcolepsy is narcolepsy associated with cataplexy.

7. A method of treating as claimed in claim 4, wherein narcolepsy is narcolepsy not associated with cataplexy.

8. A method of treating as claimed in claim 4, wherein narcolepsy is narcolepsy due to medical condition.

9. A method of treating excessive daytime sleepiness as claimed in claim 1, comprising administering to a patient in need thereof, a therapeutically effective amount of N-[4-(1-Cyclobutylpiperidin-4-yloxy)phenyl]-2-(morpholin-4-yl)acetamide dihydrochloride.

10. A method of treating excessive daytime sleepiness as claimed in claim 9, wherein the excessive daytime sleepiness is associated with narcolepsy, obstructive sleep apnea, restless leg syndrome, REM behavior disorder, posttraumatic stress disorder, autism, Down syndrome, periodic limb movements in sleep, menstrual-related hypersomnia or Kleine-Levin syndrome, comprising administering to a patient in need thereof, a therapeutically effective amount of N-[4-(1-Cyclobutylpiperidin-4-yloxy)phenyl]-2-(morpholin-4-yl)acetamide dihydrochloride.

11. A method of treating circadian rhythm sleep disorders as claimed in claim 1, comprising administering to a patient in need thereof, a therapeutically effective amount of N-[4-(1-Cyclobutylpiperidin-4-yloxy)phenyl]-2-(morpholin-4-yl)acetamide dihydrochloride.

12. A method of treating circadian rhythm sleep disorders as claimed in claim 11, wherein circadian rhythm sleep disorder is selected from irregular sleep-wake type, jet lag type or shift work type, comprising administering to a patient in need thereof, a therapeutically effective amount of N-[4-(1-Cyclobutylpiperidin-4-yloxy)phenyl]-2-(morpholin-4-yl)acetamide dihydrochloride.

13. A method of treating sleep and vigilance disorders associated with Parkinson's disease, multiple sclerosis, dementia or attention deficit hyperactivity disorder as claimed in claim 1, comprising administering to a patient in need thereof, a therapeutically effective amount N-[4-(1-Cyclobutylpiperidin-4-yloxy)phenyl]-2-(morpholin-4-yl)acetamide dihydrochloride.

14. The method of treating sleep and vigilance disorders associated with dementia as claimed in claim 1, wherein the dementia is selected from Lewy body dementia, vascular dementia, senile dementia, dementia due to Alzheimer's disease, dementia due to Parkinson's disease and/or Frontotemporal dementia.

15. The method of treating as claimed in claim 5, wherein narcolepsy is narcolepsy associated with cataplexy.

16. The method of treating as claimed in claim 5, wherein narcolepsy is narcolepsy not associated with cataplexy.

17. A method of treating excessive daytime sleepiness as claimed in claim 1, wherein the excessive daytime sleepiness is associated with narcolepsy, obstructive sleep apnea, restless leg syndrome, REM behavior disorder, posttraumatic stress disorder, autism, Down syndrome, periodic limb movements in sleep, menstrual-related hypersomnia or Kleine-Levin syndrome, comprising administering to a patient in need thereof, a therapeutically effective amount of N-[4-(1-Cyclobutylpiperidin-4-yloxy)phenyl]-2-(morpholin-4-yl)acetamide or a pharmaceutically acceptable salt thereof.

* * * * *